United States Patent
Gartner et al.

(10) Patent No.: US 6,260,561 B1
(45) Date of Patent: Jul. 17, 2001

(54) METHOD FOR USING ALIPHATIC AMINES AS CLEANERS FOR SWIMMING POOLS

(75) Inventors: Charles D. Gartner; Lisa M. Cooke, both of Midland; Debra G. Mendrick, Mount Pleasant; George A. Paul, Midland, all of MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/133,867

(22) Filed: Aug. 13, 1998

(51) Int. Cl.$^7$ .................................. B08B 9/00; A01N 2/08
(52) U.S. Cl. ........................................................ 134/22.16
(58) Field of Search ............................ 134/22.16; 422/28

(56) References Cited

U.S. PATENT DOCUMENTS

| | | | |
|---|---|---|---|
| 2,393,293 | * | 1/1946 | Corley ................................. 210/23 |
| 2,878,155 | * | 3/1959 | Crickshank ........................ 167/22 |
| 3,125,486 | * | 3/1964 | Essen et al. ....................... 167/22 |
| 3,140,976 | * | 7/1964 | Berenschot et al. ............. 167/22 |
| 3,247,053 | | 4/1966 | Hodge et al. ..................... 167/22 |
| 4,139,560 | * | 2/1979 | Reinehr et al. ................ 260/570.8 |
| 4,304,590 | * | 12/1981 | Grade et al. ........................ 71/67 |
| 4,906,651 | | 3/1990 | Hsu .................................. 514/372 |
| 5,565,021 | * | 10/1996 | Vanlaer ............................... 106/1 |
| 5,776,352 | * | 7/1998 | Vanlaer ........................... 210/749 |
| 5,935,518 | * | 8/1999 | Richard et al. ..................... 422/28 |

FOREIGN PATENT DOCUMENTS 0 364 739 A2    4/1990   (EP).
0 533 552 A1    3/1993   (EP).

OTHER PUBLICATIONS

Chemical Abstract, 91–283734/39, "Novel biocidal cpds. used with betaine surfactant—obtd. e.g. by reacting iso–decyl:oxy:propyl di amino:propane with crotonic acid and neutralising with hydrochloric acid", GB 2242–190–A.

Chemical Abstract, 116:129614w, "Preparation of amino acids and amines as biocides", GB 2,242,190.

* cited by examiner

*Primary Examiner*—Randy Gulakowski
*Assistant Examiner*—Yolanda E. Wilkins

(57) ABSTRACT

A method for cleaning the interior surfaces of a receptacle holding a body of water comprises providing the receptacle, providing an aqueous solution having from about 1 to about 100 weight percent of an aliphatic amine or salt thereof, adding the aqueous solution to the water within the receptacle. The aliphatic amine is selected from among the following: $CH_3CH_2CH_2CH_2CH_2CH_2CH_2CH_2CH_2CH_2NH_2$, R—O—$(CH_2)_3NH_2$ and R—O—$(CH_2)_3NH(CH_2)_3NH_2$ wherein R is an aliphatic hydrocarbon having from 8 to 10 carbon atoms, R optionally having additional ether linkages such as $C_nH_{(n+1)}$—$(O—CH_2CH_2)_{n'}$, and wherein n is an integer from 8 to 10 and n' is an integer from 1 to 5. When the aqueous solution is added to the water, flocculus or precipitants are substantially not formed in the water proximate to the point of addition. Also disclosed is a swimming pool having a liner and a body of water within the liner. The body of water has from about 1 to about 100 parts per million by weight of an aliphatic amine or salt thereof.

10 Claims, 1 Drawing Sheet

METHOD FOR USING ALIPHATIC AMINES AS CLEANERS FOR SWIMMING POOLS

BACKGROUND OF THE INVENTION

The present invention relates to a method of using certain aliphatic amines for cleaning swimming pools, spas, cooling towers, and other receptacles having bodies of water therein.

Swimming pools and spas can become fouled quickly and require regular cleaning. Either or both of the retained water (body of water) and the internal surfaces of the liner can become fouled. The retained water can have suspended dirt or flocculus in it and the liner surfaces can have flocculus or insoluble deposits on them. Flocculus and insoluble deposits may form from reaction of mineral compounds present in the retained water with chemicals added periodically for maintenance, cleaning, and disinfectant purposes. Mineral compounds tend to build up over time due to evaporation of retained water, infrequent draining of retained water, and from use of fill water having elevated mineral compound content.

Cleaning swimming pools and spas, especially pools, is difficult. Cleaning usually requires draining of retained water and mechanical scrubbing of surfaces with strong cleaners. Draining retained water can be expensive and time-consuming if a large volume of water must be replenished. Scrub cleaning of liner surfaces is laborious and time consuming.

One method of cleaning swimming pools and spas is to periodically add cleaners to the water so that liner surfaces are cleaned continuously without having to drain the pool or scrub clean it. Certain halogenated compounds may be added to the water to effect cleaning as well as disinfecting. Halogenated compounds however, have proven only partially effective at periodic maintenance cleaning or continuous cleaning of the liner surfaces. Further, the use of such compounds has resulted in residual odor problems, bleaching of clothing, hair discoloration, and negative environmental impact. Certain non-halogenated amine compounds such as quaternary ammonium compounds, guanidines, biguanides and polymers thereof, have been used commercially in pools and spas but have been only partially effective in cleaning. The non-halogenated compounds have proven largely ineffective at "upset" or "curative" cleaning where there is significant buildup of deposits on the liner. The non-halogenated compounds have also tended to react with mineral compounds in retained water to form flocculus and insoluble deposits. This formation of flocculus is undesirable because it adds to the cleaning problem and creates a negative visual impression with end users. End users construe cleaners that flocculate as ineffective.

It would be desirable to have a method of continuously cleaning or curative cleaning a swimming pool, spa, or other receptacle retaining a body of water without requiring draining of the water or inducing significant formation of floc within upon addition of the cleanser.

SUMMARY OF THE INVENTION

According to the present invention, there is a method for cleaning the interior liner surfaces of a receptacle holding or retaining a body of water, comprising an aqueous solution having from about 1 to about 100 weight percent of a certain aliphatic amine or salt thereof, and adding the aqueous solution to the water within the receptacle. The aliphatic amine is selected from among the following: $C_{10}H_{21}NH_2$ and $R-O-(CH_2)_3NH_2$ and $R-O-(CH_2)_3NH(CH_2)_3NH_2$ wherein R is an aliphatic hydrocarbon having from 8 to 10 carbon atoms and R optionally has additional ether linkages such as $C_nH_{(n+1)}-(O-CH_2CH_2)_n'$ wherein n is an integer from 8 to 10 and n' is an integer from 1 to 5. When the aqueous solution is added to the water, flocculus or precipitants are substantially not formed or substantially not visible in the water even proximate to the point of addition.

Further according to the present invention, there is a swimming pool or spa comprising a liner and a body of water within the liner. The body of water has from about 1 to about 100 parts per million by weight of an aliphatic amine or salt thereof corresponding to the aliphatic amines described herein.

DETAILED DESCRIPTION OF THE INVENTION

Figure 1:
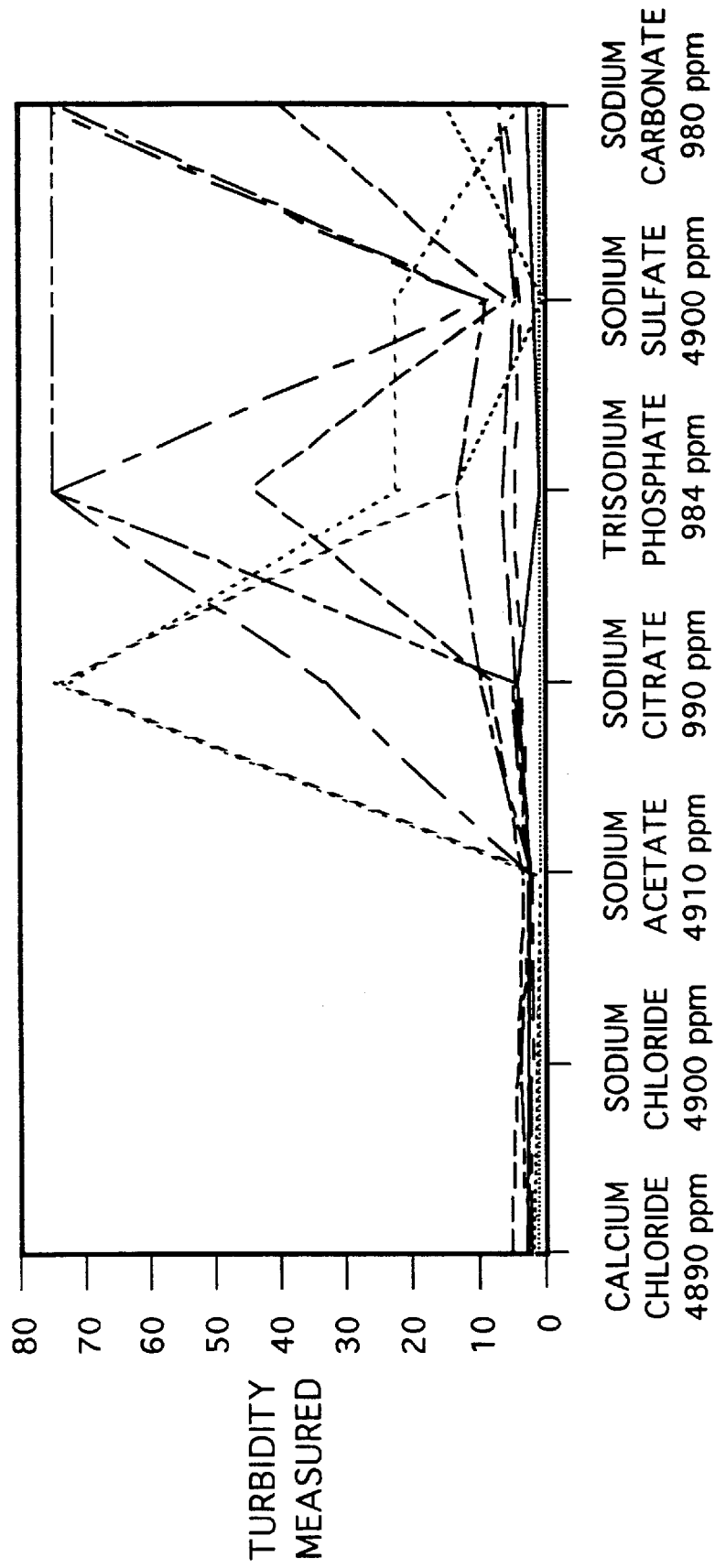
FIG. 1 is a graph representation relating to turbidity of aqueous solutions containing monovalent and/or multivalent anions and aliphatic amines useful and not useful in the present invention.

Aliphatic amines useful in the present invention include those of the following formulas:

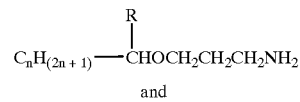

and

wherein n is an integer from 0 to 4, and R is an aliphatic hydrocarbon having from 8 to 10 carbon atoms and R optionally has additional ether linkages such as $C_nH_{(n+1)}-(O-CH_2CH_2)_n'$, wherein n is an integer from 8 to 10 and n' is an integer from 1 to 5.

Most preferred aliphatic amines are the following:

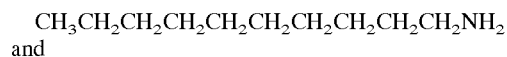
and

 and (isodecyloxypropylamine)

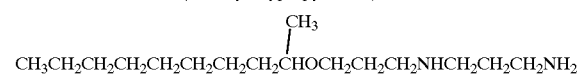

(isodecyloxypropyldiaminopropane)

The disclosed amines are very effective in continuously cleaning or curative cleaning of the liner surfaces of pools and spas. If added to the retained water of a pool or spa which has insoluble deposits or dirt on liner surfaces, the chemical and mechanical action of the dilute water/amine solution act to loosen and remove significant portions of the insoluble deposits and dirt in the form of floc. The floc is then removed by any conventional means such as by pool water filters or traps during water recirculation and/or by surface removal. The disclosed amines may also be added continuously or frequently (periodically) to the water as a preventative measure to prevent significant buildup of deposits and dirt on the liner surfaces. The disclosed amines may also be added to pools or spas having significant buildup of deposits on liner surfaces to effect upset or curative cleaning. Although not preferred, liner surfaces may also cleaned by draining the water and applying aqueous amine solutions and wiping or scrubbing the surfaces. The disclosed amines may also be added to the retained water of cooling towers or other receptacles retaining water to effect cleansing in the manner as with pools and spas.

An advantage of the disclosed amines is that they do not react to a significant degree with multivalentions commonly present in hard water to form precipitants or flocculus. Aqueous solutions of the disclosed amines can be added to pool or spa water containing multivalent ions without substantial formation of precipitants and flocculus at the point of addition. The extent of formation of precipitants or flocculus at the point of addition is substantially not visible to the naked or unaided eye. Also, aqueous solutions containing both multivalent anions and the disclosed amines are substantially free of turbidity. An aqueous solution is deemed to be substantially free of turbidity if it has a turbidity of about 10 Nephelometric Turbidity Unit (NTU) or less as measured using an HF Scientific, Inc. Turbidimeter, Model DRT 100B.

Flocculation in hard water at the point of addition of aqueous solutions of certain non-halogenated amines not of the present invention can be observed in hard water solutions containing the following: about 4910 ppm or more of sodium acetate, about 990 ppm or more of sodium citrate, about 984 ppm or more of trisodium phosphate, about 4900 ppm or more of sodium sulfate, and about 980 ppm or more of sodium carbonate, or any combination of the foregoing. Some species of non-halogenated amines not of the present invention are seen in the comparative examples. The disclosed aliphatic amines are much less likely to react with multivalent anions than the non-halogenated amines.

Salts of the disclosed amines are useful in the present method. Useful salts include those of mineral acids such as HCl or HBr and carboxylic acids such as acetic acid, propionic acid, glycolic acid, and gluconic acid. Such salts enhance the formulation and handling properties of amine solutions sold commercially in concentrates form. The salts generally have increased water solubility thereby reducing or eliminating the need for non-aqueous solvents. The salts may also enhance the handling safety of concentrated solutions by neutralizing them, thereby generally reducing corrosivity to skin.

The disclosed amines or salts thereof will typically be added to a body of water in a concentrated aqueous form preferably comprising about 0.1 to about 50 parts by weight per hundred parts by weight water (pph). Within the body of water, the disclosed amines or salts thereof will preferably be present at about 1 to about 100 parts by weight per million parts by weight water (ppm).

It is also possible to enhance the formulation stability of an aqueous solution of the amine or salt thereof by adding an organic solvent such as a alcohol having two to ten carbon atoms or a polyalkylene glycol such as propylene glycol. It is also possible to have a solution of the amine or salt thereof which is substantially or entirely in an organic solvent. Solutions having partial or substantial organic solvent content are suitable for addition to bodies of water which do not normally contact humans such as those in cooling towers.

The aqueous solutions of the disclosed amines and salts thereof can contain inert additives such as dyes, antifoaming agents, and fragrances.

The disclosed amines and salts thereof also exhibit antimicrobial activity in that they can kill or inhibit reproduction or growth of microorganisms such as fungi, bacteria, protozoa, algae and viruses.

EXAMPLES AND COMPARATIVE EXAMPLES

Examples of the present method were carried out by adding aqueous solutions of the disclosed amines (amine solutions) to aqueous solutions containing monovalent or multivalent anions (ion solutions). Comparative examples were also carried out by adding to ion solutions of amines not described herein as being useful in the present invention. A control example was also carried out wherein only water was added to the ion solutions. Turbidity of the mixtures was determined and the results compared.

The amine solutions were generally prepared according to the following: a) adding amine to water in glass jar to form a solution, shaking jar by hand for 15–20 seconds followed by shaking in a shaking device for 1 hour; b) adding 0.1 N hydrochloric acid(HCl) to the solution; c) optionally mixing in 0.1 N sodium hydroxide (NaOH) to the solution to adjust the pH of the concentrated aqueous amine solution to a pH of approximately 7 to 8; d) mixing in additional water to bring the solution to approximately 5000 ppm amine and e) shaking solution again for 15 seconds. Any deviations from the above methodology are described Table 1 below for individual samples.

Ion solutions were generally prepared by dissolving mineral compounds in water and optionally mixing in 0.1 N NaOH to adjust the pH to desirable levels. Those solutions forming monovalent anions were of calcium chloride, sodium chloride, and sodium acetate. Those solutions forming multivalent anions were sodium citrate, trisodium phosphate, sodium sulfate, and sodium carbonate.

After the ion solutions and the amine solutions were prepared, 50 milliliters (ml) of each of the ion solutions were mixed with 1 ml of each of the amine solutions. The resulting solution was shaken for about 15 seconds and then allowed to stand for one hour. Turbidity of the resulting solution was measured using an HF Scientific, Inc. Turbidimeter, Model DRT 100B. Turbidity values are set forth in Table 3. A turbidity of 10 NTU or less was considered acceptable.

None of the ion/amine solutions having monovalent anions were turbid (flocculus not formed). Thus, all of the amines, including those which were examples of the invention and those which were not, performed satisfactorily.

In ion/amine solutions having multivalent anions, only three of the amines, isodecyloxypropylamine, isodecyloxypropyl-1,2-diaminopropane, and n-decylamine, performed satisfactorily with respect to multivalent anions. Those solutions exhibited a turbidity of from 1 to less than 8 NTU.

The ion/amine solutions containing 2-ethylhexyloxypropylamine, an amine not useful in the present invention, exhibited low turbidity when added to solutions containing multivalent anions. However, that amine was not deemed useful in the present invention because it did not exhibit cleaning efficacy.

TABLE 1

Amine Solutions

| Sample Description | Wt. Amine (grams) | Wt. H$_2$O (grams) | Wt. 0.1 N HCl (grams) | Wt. 0.1 N NaOH (grams) | Wt. Additional H$_2$O (grams) | ppm Amine | Observations Concerning Sample Turbidity and Amine Solubility in Water |
|---|---|---|---|---|---|---|---|
| #1 2-ethylhexyloxypropylamine* | 0.51 | 44.16 | 27.10 | 1.08 | 31.66 | 4880 | Resulting solution was cloudy |
| #2 Isodecyloxypropylamine | 0.50 | 40.82 | 22.04 | 0 | 36.64 | 5000 | Resulting solution was clear-slightly cloudy |
| #3 Isododecyloxypropylamine* | 0.51 | 41.58 | 21.02 | 0.75 | 36.34 | 5090 | Resulting solution was clear |
| #4 Isodecyloxypropyl-1,2-diaminopropane | 0.50 | 41.70 | 34.73 | 1.50 | 21.58 | 5000 | Resulting solution was slightly cloudy |
| #5 Isododecyloxypropyl-1,2-diaminopropane* | 0.50 | 45.45 | 27.86 | 0 | 26.22 | 5000 | Resulting solution was clear |
| the sixth row, which commences with "#6 decylthioethanamine" the seventh row, which commences with #8 dodecylamine" and | | | | | | | Dodecylamine crystallized upon addition of H$_2$O, so the sample was put in an oven at 50° C. for 1 hour; then HCl and NaOH were added. Resulting solution was clear. |
| #9 tallowalkyl-(N-(3-aminopropyl)-1,3 propane diamine* | 0.50 | 42.26 | 25.30 | 0 | 32.01 | 5000 | TRT was warmed prior to use, but TRT didn't readily dissolve in water, so the sample was put in the oven at 50° C. for 1 hr and then shaken before adding HCl. Resulting solution was clear. |
| #10 coconutalkyl-1,3-propanediamine* | 0.51 | 41.34 | 32.42 | 0 | 27.31 | 5020 | DC was warmed prior to use, but DC didn't readily dissolve in water, so the DC/water was put in the oven at 50° C. for 1 hr and then shaken before adding HCl. Resulting solution was clear. |
| the tenth row, which commences with #11 n-decylamine'. | | | | | | | Decylamine didn't readily dissolve in water, so the decylamine/water was put in the oven at 50° C. for 30 minutes and then shaken before adding HCl and NaOH. Resulting solution was clear. |

*Not of the present invention.

TABLE 2

Ion Solutions

| Sample Description | Wt. of Mineral Compound | Wt. H$_2$O | Mineral Compound Concentration ppm | Wt. 0.1 N HCl (if needed) | Final Solution pH |
|---|---|---|---|---|---|
| Calcium Chloride | 5.00 | 995.1 | 4995 | 0.91 | 8.06 |
| Sodium Chloride | 5.00 | 995.0 | 5000 | 0 | 5.90 |
| Sodium Acetate | 5.01 | 995.1 | 5009 | 0 | 8.08 |
| Sodium Citrate | 1.01 | 999.0 | 1010 | 0 | 8.27 |
| Sodium Phosphate | 1.00 | 995.0 | 1004 | 0 | 11.44 |
| Sodium Sulfate | 5.00 | 995.0 | 5000 | 0 | 6.01 |
| Sodium Carbonate | 1.00 | 999.1 | 1000 | 0 | 10.81 |

TABLE 3

Turbidity Results

| Final Concentration of Amine | 4890 ppm Calcium Chloride | 4900 ppm Sodium Chloride | 4910 ppm Sodium Acetate | 990 ppm Sodium Citrate | 984 ppm Trisodium Phosphate | 4900 ppm Sodium Sulfate | 980 ppm Sodium Carbonate |
|---|---|---|---|---|---|---|---|
| 96 ppm 2-ethylhexyloxypropylamine* | 1.94 | 0.79 | 0.84 | 2.82 | 0.269 | 2.23 | 2.9 |
| 98 ppm Isodecyloxypropylamine | 2.67 | 0.56 | 1.06 | 2.19 | 5.02 | 2.14 | 5.52 |
| 100 ppm Isododecyloxypropylamine* | 4.65 | 2.29 | 1.3 | 8.8 | 45.4 | 5.8 | 42 |

TABLE 3-continued

Turbidity Results

| Final Concentration of Amine | 4890 ppm Calcium Chloride | 4900 ppm Sodium Chloride | 4910 ppm Sodium Acetate | 990 ppm Sodium Citrate | 984 ppm Trisodium Phosphate | 4900 ppm Sodium Sulfate | 980 ppm Sodium Carbonate |
|---|---|---|---|---|---|---|---|
| 98 ppm Isodecyloxypropyl-1,2-diaminopropane | 2.24 | 0.57 | 0.63 | 3.71 | 7.57 | 4.5 | 7.53 |
| 98 ppm Isododecyloxypropyl-1,2 = diaminopropane* | 2.93 | 1.23 | 0.6 | 10.4 | 13 | 8.55 | 75 |
| 98 ppm decylthioethanamine* | 1.86 | 0.68 | 0.62 | 32.6 | 75 | 9 | 75 |
| 98 ppm Dodecylamine* | 3.21 | 3.22 | 1.58 | 4.5 | 75 | 75 | 75 |
| 98 ppm tallowalkyl-(N-(3-aminopropyl)-1,3 propane diamine* | 0.93 | 0.24 | 0.19 | 75 | 12.7 | 0.32 | 14.2 |
| 98 ppm coconutalkyl-1,3-propanediamine* | 1.56 | 0.53 | 0.57 | 75 | 21.6 | 22.9 | 2.74 |
| None (Control?) | 0.7 | 0.09 | 0.15 | 0.18 | 0.16 | 0.1 | 0.1 |
| 98 ppm Decylamine* | 1.16 | 0.37 | 0.5 | 0.5 | 4.1 | 0.47 | 1.26 |

*Not of the present invention.

What is claimed is:

1. A method for cleaning the interior surfaces of a receptacle retaining a body of water, comprising:
   a) providing the receptacle;
   b) providing an aqueous solution having from about 015 to about 100 weight percent of an aliphatic amine of any of the following formulas or a salt of any thereof:

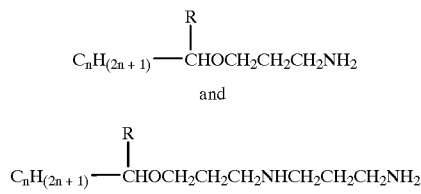

and $$C_nH_{(2n+1)}\!\!-\!\!\overset{R}{\underset{|}{C}}HOCH_2CH_2CH_2NHCH_2CH_2CH_2NH_2$$

wherein n is an integer from 0 to 4 and R is an aliphatic hydrocarbon having from 8 to 10 carbon atoms and R optionally has additional ether linkages; and
   c) adding the aqueous solution to the water within the receptacle wherein flocculus or precipitants are substantially not formed in the water proximate to the point of addition as the aqueous solution is added.

2. The method of claim 1, wherein the aliphatic amine is isodecyloxypropylamine.

3. The method of claim 1, wherein the aliphatic amine is isodecyloxypropyldiaminopropane.

4. The method of claim 1, wherein the receptacle has hard water therein comprising multivalent anions.

5. The method of claim 4, wherein the multivalent anion in solution is selected from the group consisting of citrate, phosphate, sulfate, carbonate, and any combination of the foregoing.

6. The method of claim 1, wherein the receptacle is a swimming pool.

7. The method of claim 2, wherein the receptacle is a swimming pool.

8. The method of claim 3, wherein the receptacle is a swimming pool.

9. The method of claim 1, wherein the receptacle is a spa.

10. The method of claim 1, wherein the receptacle is a cooling tower.

* * * * *